(12) United States Patent
Bernhardt et al.

(10) Patent No.: US 7,298,823 B2
(45) Date of Patent: Nov. 20, 2007

(54) METHOD AND DEVICE FOR USER-SPECIFIC PARAMETERIZATION OF AN X-RAY DEVICE

(75) Inventors: Philipp Bernhardt, Forchheim (DE); Marcus Pfister, Bubenreuth (DE); Rudolf Sollacher, Eching (DE); Volker Tresp, Müchen (DE)

(73) Assignee: Siemens Aktiengesellschaft, Munich (DE)

( * ) Notice: Subject to any disclaimer, the term of this patent is extended or adjusted under 35 U.S.C. 154(b) by 85 days.

(21) Appl. No.: 11/170,661

(22) Filed: Jun. 29, 2005

(65) Prior Publication Data

US 2006/0002513 A1    Jan. 5, 2006

(30) Foreign Application Priority Data

Jun. 30, 2004    (DE) ...................... 10 2004 031 681

(51) Int. Cl.
*H05G 1/30* (2006.01)
(52) U.S. Cl. ...................... 378/97; 378/98.5
(58) Field of Classification Search ................. 378/62, 378/108–112, 95–97, 98.8, 165, 115, 98, 378/98.2, 98.5, 98.7; 382/128, 132
See application file for complete search history.

(56) References Cited

U.S. PATENT DOCUMENTS 5,371,777 A * 12/1994 Koehler et al. ............. 378/108
6,813,365 B1 * 11/2004 Funahashi ................... 382/100
2003/0118154 A1   6/2003 Maack et al.

FOREIGN PATENT DOCUMENTS

DE    101 61 708 A1    6/2003

* cited by examiner

*Primary Examiner*—Hoon Song

(57) ABSTRACT

A method and a suitable x-ray device (1) for carrying out the method are specified for effective and operationally simplified user-specific optimization of a parameter configuration (K) of an x-ray device (1), said configuration comprising at least one recording parameter (U,I,t,F). It is accordingly provided that a user (20) is shown a plurality of reference images (V,V1) for different reference parameter sets (PV) from a reference memory (21) in which are stored a large number of reference images (V,V0) each with an associated reference parameter set (PV), that for each reference image (V,V1) shown the user (20) submits an assessment (BM) of the image quality (V,V1), and that on the basis of the submitted assessments (BM) an optimized parameter configuration (K) is created from the reference parameter sets (PV) of the reference images (V,V1) shown.

12 Claims, 2 Drawing Sheets

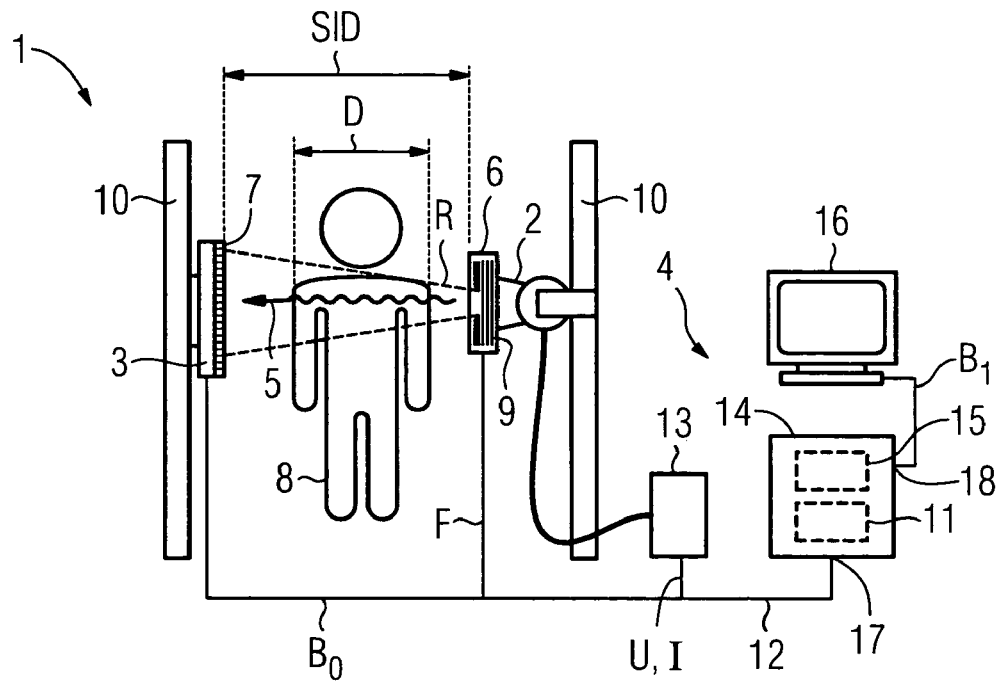
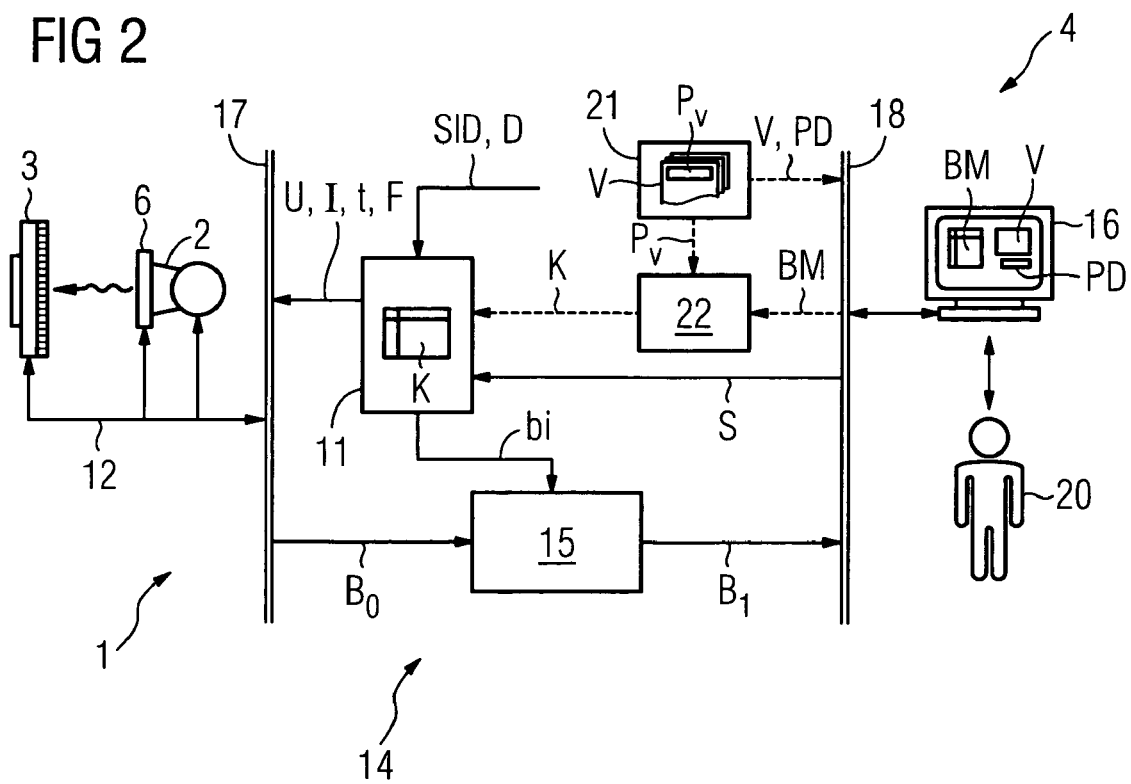

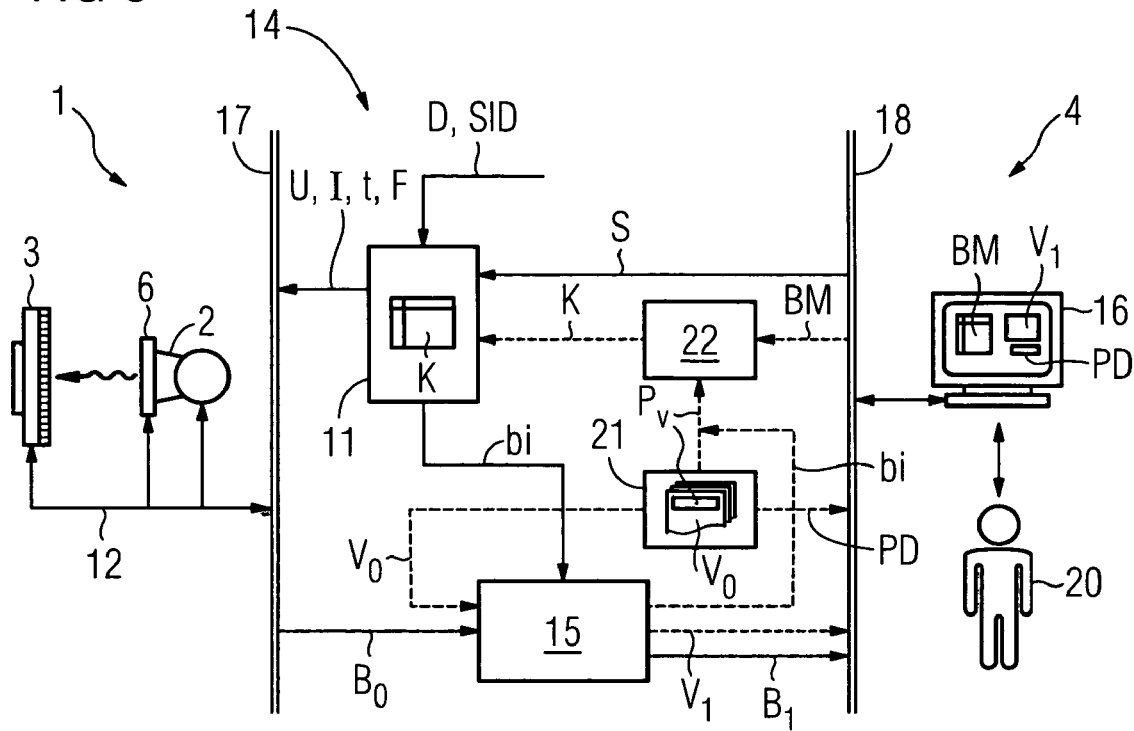
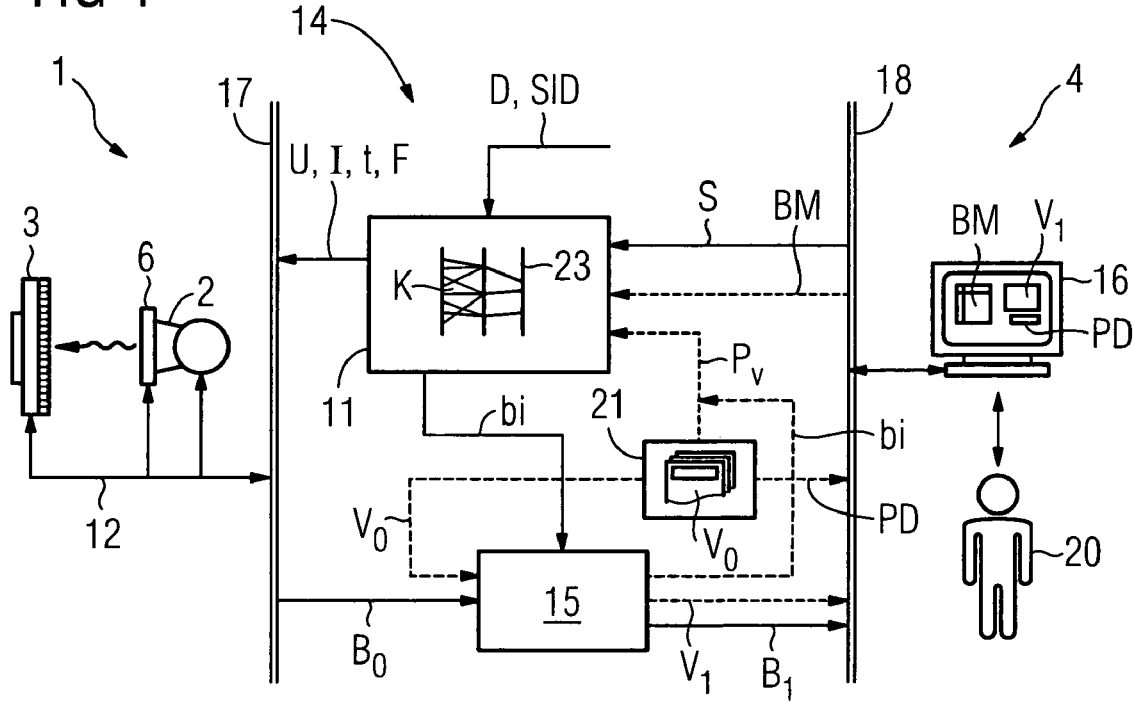

METHOD AND DEVICE FOR USER-SPECIFIC PARAMETERIZATION OF AN X-RAY DEVICE

CROSS REFERENCE TO RELATED APPLICATIONS

This application claims priority to the German application No. 10 2004 031 681.3, filed Jun. 30, 2004 which is incorporated by reference here in in its entirety.

FIELD OF INVENTION

The invention relates to a method for user-specific parameterization of an x-ray device designed in particular for angiographic and/or cardiological examinations according to the pre-characterizing clause of claim 1, and to an associated x-ray device according to the pre-characterizing clause of claim 8.

BACKGROUND OF INVENTION

For medical x-ray examinations in angiography and cardiology, excellent image quality is of particular importance in order to be able to differentiate clearly between the comparatively weakly absorbing structures being examined, in particular tissue and vessels as well as any catheters and stents present, in the body of a patient. At the same time, however, care must be taken to ensure that the patient and the medical personnel are exposed to as low an x-ray dose as possible.

The quality of a medical x-ray image depends on a large number of adjustable parameters. These parameters include, on the one hand, recording parameters, i.e. parameters such as those affecting the recording conditions obtaining during imaging. These include in particular the voltage and current density of the supply voltage for the x-ray radiator as well as the exposure time and the setting of an x-ray filter. The quality of an x-ray image is additionally affected by variables generally dictated by the examination conditions. These include in particular the patient thickness, i.e. the thickness of the irradiated body tissue and the radiator/detector spacing (also known as the source-image distance, or SID for short).

In more recent times, instead of conventional radiography employing x-ray films, digital x-ray diagnostic techniques in which the recorded x-ray image is present in electronic format, i.e. in the form of digital image data, have found widespread use. This makes it possible for the x-ray image to be post-processed using electronic image processing means before it is displayed on a screen. For a digital x-ray device it is therefore necessary to adjust not only the recording parameters but also a number of image processing parameters which affect the way in which the image is post-processed by the x-ray equipment and in turn the image quality.

SUMMARY OF INVENTION

It is known to control the recording parameters as a function of measurable input variables, e.g. the detector input dose, in such a way that comparable image quality is achieved under different examination conditions. For an x-ray device of this kind, a parameter configuration in which characteristics of the recording parameters are stored as a function of the input variables is generally predefined. These characteristics have hitherto been determined by the manufacturer on the basis of phantom measurements or simulation calculations.

The problem here is that the image quality does not constitute an objectively measurable variable, but is subject to the subjective impression of the treating radiologist. The visual impression expected and experienced as optimum is largely dictated by the taste or school of an x-ray department or even by the trained knowledgeability of an individual radiologist and therefore generally differs considerably from radiologist to radiologist.

Changing the parameter configuration of an x-ray device has hitherto been performed by technical support staff, especially as the x-ray equipment user, i.e. the treating physician, generally lacks the necessary specialist knowledge about how image quality is affected by varying the parameters. Adapting the parameter configuration to suit the individual user would therefore involve considerable cost and/or complexity, particularly as different parameter configurations would also have to be provided as part of so-called organ programs for each body organ to be recorded, each recording projection and possibly different objects to be detected (body tissue, vessels or artificial implants such as catheters or stents), and this does not therefore usually take place.

In order nevertheless to allow user-specific adaptation of the recording parameters of an x-ray device with comparatively low overhead in terms of cost and/or complexity, there is provided according to DE 101 61 708 A1 a first memory arrangement in which there is stored a number of recording parameter sets, one of which can be selected by a user in order to take an X-ray. The resulting and possibly user-modifiable recording parameters are stored in a second memory arrangement. According to DE 101 61 708 A1, there are additionally provided means embodied to evaluate the second recording parameter sets which are assigned to the same first recording parameter set and to derive from them a new recording parameter set which is stored in place of the first recording parameter set in the first memory arrangement.

An object of the present invention is to specify a method that is effective and simplified in terms of handling complexity for user-specific parameterization of an x-ray device in respect of the parameters affecting image quality. It is also an object of the invention to specify a device which is suitable for performing said method.

The object is achieved by the claims.

Accordingly, a user is shown a plurality of reference images in order to parameterize a parameter configuration containing at least one recording parameter, in particular the tube voltage, the tube current, the exposure time and/or a filter setting. These reference images corresponding to the x-ray images that can be generated by the x-ray device are held in a reference memory of the x-ray device, there being stored for each reference image a corresponding reference parameter set specifying the conditions under which the reference image has been produced. In particular, the reference parameter set includes the settings of the recording parameters obtaining at the time the reference image was recorded and also, if the reference image has undergone post-processing, the corresponding image processing parameters. The reference parameter set additionally includes other variables associated with the reference image, in particular the patient thickness, SID and patient dose.

In order to determine the user's subjective visual impression, according to the method the user is prompted by the x-ray device to assess each displayed reference image according to predefined criteria. On the basis of these assessments, an optimized parameter configuration is then created from the reference parameter sets of the displayed reference images and stored.

Specifically a user's subjective visual impression is automatically analyzed by the method and the x-ray device operating in accordance therewith, and the image quality is optimized in respect of the individual requirements of that user. A considerable advantage of the method is that it can be carried out intuitively on the part of the user. In other words, the user can perform image optimization using the method alone, without his requiring prior knowledge regarding the effect of particular parameters on image quality in order to do so. For x-ray device parameterization according to the invention, technical support staff are not therefore required, or only to a comparatively small extent, thereby reducing the cost overhead associated with putting the x-ray device into operation.

Image optimization according to the method is particularly effective, moreover, in that it commences as early as the image recording stage rather then during post-processing of already existing x-ray images. This means that particularly good image quality can be achieved while at the same time minimizing the patient dose.

In a preferred embodiment of the method, not only the recording parameters but also at least one image processing parameter is optimized which is likewise contained in the parameter configuration of the x-ray device. For this purpose the user is presented with reference images which have been post-processed differently, i.e. whose assigned reference parameter sets differ in the one or more image processing parameters, so that the user also includes image post-processing in the assessment.

In a variant of the invention, the reference images are already stored in post-processed form in the reference memory. In another variant, the reference images are stored in unprocessed form in the reference memory and are only modified for display purposes in an image post-processing unit of the x-ray device. Likewise the corresponding image processing parameters are in this case not added to the reference parameter set assigned to a reference image until the method is applied. The particular advantage of this last mentioned variant is that it is only necessary to provide a comparatively small number of reference images which can be flexibly subjected to any post-processing as required.

When assessing the reference images, the doctor is preferably given an impression of the radiation load to be expected for the patient and the medical personnel, particularly therefore himself, in that the user is also shown the underlying patient dose together with a reference image.

In order to ensure comparable image quality under different examination conditions, it is also expediently provided that at least one parameter contained in the parameter configuration is predefined as a function of at least one input variable, a preferable input variable being the patient thickness and/or the source-image distance (SID) and/or the detector input dose and/or the contrast-to-noise ratio. The dependence of one parameter on the one or more input variables is implemented in one embodiment of the invention by defining the parameter as a characteristic, mathematical function, node table, etc. of the at least one input variable. It is alternatively provided for the dependence of the parameter or parameters of the parameter configuration on the input variable or variables to be mapped onto the connections of a neural network.

When creating the optimized parameter configuration from the reference parameter sets of the reference images shown and assessed, it is preferably provided, as part of weighted averaging over the reference parameter sets, for only parameter sets or preferably such parameter sets as are comparable in respect of the absolute value of the input variables to be linked, so that when considering a sufficient number of reference images the characteristics of the parameters can be established as a function of the input variables. If the parameter configuration is constructed as a neural network, it is provided for the latter to be trained in the course of optimization by the reference parameter sets of the reference images shown and by the assigned assessments.

In addition or alternatively it is provided that at least one parameter of the parameter configuration be defined as a function of an abstract image quality measure, on the basis of which a user can adjust the subjective image quality corresponding to his expectations continuously or in discrete steps. This subjective image quality measure, hereinafter also referred to as a control variable, is preferably derived from standardized subjective assessment criteria on the basis of which the user assesses the reference images. Assessment criteria provided are in particular the resolution, the noise impression (in contrast to the objectively determinable signal-to-noise ratio), the visibility of details and/or the contrast.

BRIEF DESCRIPTION OF THE DRAWINGS

Exemplary embodiments of the invention will now be explained in greater detail with reference to the accompanying drawings, in which:

FIG. 1 schematically illustrates an x-ray device with an x-ray radiator, a digital x-ray detector and a control and evaluation system, FIG. 2 is a schematic block diagram of a first embodiment of the device according to FIG. 1, FIG. 3 shows in the manner of FIG. 2 a second embodiment of the device according to FIG. 1, and FIG. 4 shows in the manner of FIG. 2 a third embodiment of the device according to FIG. 1.

DETAILED DESCRIPTION OF INVENTION

Mutually corresponding parts and variables are consistently denoted by the same reference characters in all the figures.

The medical x-ray device 1 schematically illustrated in FIG. 1 comprises an x-ray radiator 2, a digital x-ray detector 3 (hereinafter referred to as a detector for short) as well as a control and evaluation system 4. A collimator 6 and an anti-scatter grid 7 are interposed in a radiation direction 5 between the x-ray radiator 2 and the detector 3.

The collimator 6 is used to extract from the x-radiation R produced by the x-ray radiator 2 a sub-beam of a required size which passes through a patient under examination 8 or an object under examination and the anti-scatter grid 7 and is incident on the detector 3. The collimator 6 additionally contains a filter arrangement 9 by means of which the x-radiation R generated by the x-ray radiator 2 can be attenuated and/or modified in respect of its spectral distribution. The filter arrangement 9 is adjustable particularly in respect of its filter thickness F. The anti-scatter grid 7 is used to mask out stray radiation which is incident on the detector 3 at a shallow angle and which would corrupt an x-ray image $B_0$ recorded by the detector 3.

The x-ray radiator 2 and the detector 3 are displaceably fixed to a stand 10 or above and below an examination table.

The control and evaluation system 4 comprises a control unit 11 for controlling the x-ray generator 2 and the detector 3. The control unit 11 is connected via a data line 12 to an x-ray generator 13 which generates an electrical supply voltage for radiation generation and feeds it out to the x-ray radiator 2. The absolute voltage value (hereinafter referred to as tube voltage U) and the current intensity (hereinafter referred to as tube current I) of the supply voltage and likewise the exposure time t are set by the control unit 11 and predefined as recording parameters for the x-ray generator 13. The filter thickness F is also set by the control unit 11 and predefined as a recording parameter for the collimator 6.

The control unit 11 is a software component of a data processing system 14 comprising as a further software component an image processing unit 15 for post-processing a digital x-ray image B (also termed raw image) produced by the detector 3 and transmitted to the data processing system 14 via the data line 12. The data processing system 14 preferably comprises further software components for evaluating findings and displaying the post-processed x-ray images $B_1$.

For data input and output, particularly for displaying x-ray images $B_1$ and for entering control and processing commands, the data processing system 14 is connected to peripheral devices 16, in particular a screen, keyboard, mouse, printer, etc.

FIG. 2 shows the device 1 in a schematic block diagram in which in particular the structure of the data processing system 14 is depicted in greater detail. Two interfaces 17 and 18 via which the data processing system 14 communicates with the x-ray radiator 2, the detector 3 and the collimator 6 on the one hand and with the peripheral devices 16 on the other are indicated in FIG. 2 by vertical double lines in each case.

During normal operation of the x-ray device 1, the control unit 11 controls both the generation of x-ray images $B_0$ and their post-processing by the image processing unit 15. For this purpose the control unit 11 has at its disposal a parameter configuration K containing on the one hand the recording parameters U, I, t and F and, on the other, a number of image processing parameters $b_i$ (i=1,2,3 ...). Depending on the latter, the image processing unit 15 uses conventional digital image processing methods to perform a predefined modification on the unprocessed x-ray images $B_0$. Such methods include, for example, the pixel-by-pixel application of characteristics for color or brightness modification of the x-ray image, filtering operations such as applying a low-pass, high-pass or median filter, frequency band-dependent filtering, contrast or brightness operations (also known as windowing) or similar.

The recording parameters U, I, t and F and the image processing parameters $b_i$ are stored as part of the parameter configuration K in the form of characteristics U(S,D,SID), I(S,D,SID), t(S,D,SID), F(S,D,SID) and $b_i$ (S,D,SID) which are a function of the input variables source-image distance SID and patient thickness D. The characteristics of the parameters U, I, t, F and $b_i$ contained in the parameter configuration K are additionally formulated as a function of a control parameter S. The control parameter S is a signal whose absolute value is a subjective measure of image quality and which can be varied in discrete steps or continuously by a user 20 via the peripheral devices 16 in order to set a high or low image quality as required.

To record an x-ray image $B_0$, the control unit 11 determines concrete values for the recording parameters U, I, t, F and the image processing parameters $b_i$ on the basis of a predefined combination of input variables S, D, SID and of the predefined characteristics U(S,D,SID), I(S,D,SID), t(S,D,SID), F(S,D,SID) and $b_i$(S,D,SID) and makes them available to the x-ray radiator 2, the detector 3 and the collimator 6 or, as the case may be, to the image processing unit 15.

User-specific adaptation of the parameter configuration K takes place in an optimization phase preceding normal operation of the x-ray device 1, in particular during commissioning. However, the user 20 can likewise initiate the optimization phase at any subsequent point in time, particularly if he feels that the current parameter configuration K of the x-ray device 1 is unsatisfactory.

In order to carry out the optimization phase, the data processing system 14 of the x-ray device 1 incorporates a reference memory 21 and an optimization unit 22, the latter in turn being implemented as a software component of the data processing system 14. Method steps involved in the optimization phase are indicated by dashed arrows in the diagram shown in FIG. 2.

In the reference memory 21 there are stored a large number of reference images V, each reference image V being assigned an associated reference parameter set $P_V$. The reference images V are x-ray images preferably originating from anonymized medical studies on a system corresponding to the x-ray device 1. The assigned reference parameter set $P_V$ in each case contains the values of the recording parameters U, I, t, F which were set at the time the relevant reference image V was recorded. The reference parameter set $P_V$ additionally contains information about the source-image distance SID, the patient thickness D and the patient dose PD associated with the recording of the reference image V.

The reference images V stored in the reference memory 21 are selected such that the parameter space spanned by the recording parameters U, I, t, F is as fully covered as possible; in other words, so that the reference images V constitute a representative selection of all the possible value combinations of the recording parameters U, I, t, F.

For the embodiment of the x-ray device 1 shown in FIG. 2, the reference memory 21 already contains post-processed reference images V. The reference parameter set $P_V$ assigned to the particular reference image V therefore also includes the value of all the image processing parameters $b_i$ according to which the reference image V has been post-processed, the reference images V stored in the reference memory 21 being selected such that the region of the parameter space spanned by the image processing parameters $b_i$ is also covered.

To sum up, the reference parameter set $P_V$ contains all the parameter values which characterize the corresponding reference image V.

In the optimization phase, a number of the reference images V stored in the reference memory 21 are now displayed to the user 20 via the peripheral devices 16. In order to give the user 20 an impression of the radiation load associated with the image recording, the user 20 is simultaneously shown the patient dose PD associated with the reference image V. The user 20 is additionally shown a standardized assessment matrix BM on the basis of which the user 20 assesses the reference image V displayed. The assessment matrix BM comprises a number of predefined assessment criteria, preferably those of resolution, noise impression, visibility of details and contrast, as well as, for each criterion, an assessment scale from 1 to 5 on which the user 20 rates the extent to which the relevant criterion is met by the reference image V displayed.

When the user 20 has completed the assessment matrix BM, it is transferred to the optimization unit 22 which additionally accesses the reference parameter set $P_V$ of the corresponding reference image V in question.

The optimization unit 22 now links the corresponding reference parameter sets $P_V$ according to the submitted assessment matrices BM, thereby generating an optimized parameter configuration K which is then transmitted by the optimization unit 22 to the control unit 11 where it is stored in place of the previous parameter configuration K.

In the embodiment according to FIG. 2, this linking is performed by the optimization unit 22 in the form of a parameter-specific, weighted averaging over the recording parameters U,I,t,F and the image processing parameters $b_i$ of the reference parameter sets $P_V$, said averaging being understood to be one in which the average is always taken over mutually corresponding parameters of the various parameter sets. The weighting factors are derived from the assessment matrices BM. The weighting is additionally performed in such a way that averaging takes place only or preferably over parameter sets $P_V$ which are comparable in respect of the source-image distance SID, the patient thickness D and control parameter S. For this purpose the control parameter S to be assigned to a reference image V is determined via weighted averaging over the assessment criteria of the relevant assessment matrix BM.

In this way the optimization unit 22 determines nodes for the characteristics U(S,D,SID), I(S,D,SID), t(S,D,SID), F(S,D,SID) and $b_i$(S,D,SID) of the optimized parameter configuration K. The optimization unit 22 interpolates between these nodes if necessary by means of suitable fit algorithms, etc.

In a variant, as shown in FIG. 3, of the x-ray device 1, unprocessed reference images $V_0$ corresponding to the unprocessed x-ray images $B_0$ (i.e. raw images) generated by the detector 3 are stored in the reference memory 21. The reference parameter set P v assigned to these reference images $V_0$ in each case accordingly contains initially only parameter values of the recording parameters U, I, t, F as well as source-image distance SID, but no explicit values for image processing parameters $b_i$. In this embodiment of the x-ray device 1, post-processing of the reference images $V_0$ is not carried out until the optimization phase. It is performed by first feeding each reference image $V_0$ to the image processing unit 15 where it is modified in accordance with predefined image processing parameters $b_i$. Only the modified reference image $V_1$ is then displayed to the user 20 via the peripheral devices 16. The corresponding values of the image processing parameters $b_i$ are correspondingly not added to the associated reference parameter set $P_v$ until the optimization phase. Assessment of the reference images $V_1$ by the user 20 and optimization of the parameter configuration K by the optimization unit 22 take place as described above.

In another variant, as shown in FIG. 4, of the x-ray device 1, the parameter configuration K is not provided in the form of concrete characteristic data, but is represented by the connections of a neural network 23 implemented as p art of the control unit 11. This neural network 23 is trained in the optimization phase using the reference parameter sets $P_V$ of the reference images V shown and the assessment matrices BM submitted by the user 20 for this purpose, thereby "learning" which combinations of the recording parameters U, I, t, F and image processing parameters $b_i$ of the user 20 are preferred for a predefined combination of the input variables S, D, SID.

In practice, the x-ray device 1 does not contain only a single parameter configuration K, but a separate parameter configuration K assigned to each of a plurality of organ programs, the parameter configuration K provided in an organ program being optimized for the representation of a particular body organ in a particular recording projection and possibly for the representation of a particular structure or substance (e.g. vessels, tissue, catheters, stents or iodine as a contrast medium). In respect of this optimization, there are stored in the reference memory 21 a separate series of reference images V or $V_0$ for each organ program.

It is additionally provided that the x-ray device 1 incorporates a plurality of user profiles as part of which there are in turn stored in each case a separate user-specific parameter configuration K or a plurality of user- and organ program-specific parameter configurations K.

What is claimed is:

1. A method for optimizing an operating parameter set related to an imaging quality of an x-ray device, the method comprising:
    displaying reference images stored in a reference memory and corresponding to different reference operating parameter sets, the reference memory including a plurality of reference images and a plurality of corresponding reference operating parameter sets;
    evaluating each displayed reference image by a user regarding an image quality of the displayed reference image; and
    generating an optimized operating parameter set based upon the evaluations and the reference parameter sets corresponding to the displayed reference images.

2. The method as claimed in claim 1, wherein the operating parameter set includes at least one image processing parameter, and post-processed reference images corresponding to different settings of the image processing parameter are displayed for supporting the evaluations.

3. The method as claimed in claim 1, wherein the operating parameter set includes an imaging-related parameter chosen from the group consisting of an x-ray tube voltage, an x-ray tube current, an exposure time, and a filter setting.

4. The method as claimed in claim 1, wherein a patient radiation dose corresponding to each displayed reference image is displayed.

5. The method as claimed in claim 1, wherein the operating parameter set includes at least one operating parameter stored in the reference memory as a function of an element chosen from the group consisting of a thickness of a patient, a distance between an x-ray source and an x-ray detector of the x-ray device, an x-ray detector input dose, and a contrast-to-noise ratio.

6. The method as claimed in claim 1, wherein the evaluations are based on a subjective assessment criterion.

7. The method as claimed in claim 6, wherein the subjective assessment criterion is a criterion chosen from the group consisting of an image resolution, an image noise, a visibility of image details, and an image contrast.

8. The method as claimed in claim 6, wherein the operating parameter set includes at least one operating parameter stored in the reference memory as a function of an image quality measure derived from the assessment criterion.

9. An x-ray device, comprising:
    an x-ray radiation source;
    a collimator arranged downstream the x-ray radiation source relative to a radiation direction;
    an x-ray detector for recording a digital x-ray image; and
    a control and evaluation device for selecting at least one imaging parameter included in an operating parameter set and for controlling the x-ray radiation source, the x-ray detector or the collimator based upon the selected imaging parameter, wherein the control and evaluation device is configured to:

display reference images stored in a reference memory and corresponding to different reference operating parameter sets, the reference memory including a plurality of reference images and a plurality of corresponding reference operating parameter sets;

receive from a user an evaluating related to each displayed reference image, the evaluation regarding an image quality of the displayed reference image; and generate an optimized operating parameter set based upon the evaluations and the reference operating parameter sets corresponding to the displayed reference images.

10. The x-ray device as claimed in claim 9, wherein the control and evaluation device:

includes an image processing unit configured to post-process an x-ray image recorded by the x-ray detector using an image processing parameter included in the operating parameter set, and is configured to display post-processed reference images corresponding to different settings of the image processing parameter for supporting the evaluations.

11. The x-ray device as claimed in claim 9, wherein the operating parameter set is included in a neural network, and the control and evaluation device is configured to train the neural network for optimizing the operating parameter configuration based on the reference operating parameter sets corresponding to the displayed reference images and the evaluations.

12. The x-ray device as claimed in claim 9, wherein the control and evaluation device comprises an optimization unit for optimizing the operating parameter set, the optimization unit configured to perform a weighted averaging over the reference operating parameter sets corresponding to the displayed reference images, the weighted averaging based on the evaluations.

* * * * *